US006984626B2

United States Patent
Nadin et al.

(10) Patent No.: US 6,984,626 B2
(45) Date of Patent: Jan. 10, 2006

(54) GAMMA-SECRETASE INHIBITORS

(75) Inventors: Alan John Nadin, Sawbridgeworth (GB); Graeme Irvine Stevenson, Saffron Waldøn (GB)

(73) Assignee: Merck, Sharp & Dohme Ltd., Hoddesdon (GB)

( * ) Notice: Subject to any disclaimer, the term of this patent is extended or adjusted under 35 U.S.C. 154(b) by 461 days.

(21) Appl. No.: 10/257,058

(22) PCT Filed: Apr. 4, 2001

(86) PCT No.: PCT/GB01/01549

§ 371 (c)(1),
(2), (4) Date: Oct. 7, 2002

(87) PCT Pub. No.: WO01/77144

PCT Pub. Date: Oct. 18, 2001

(65) Prior Publication Data

US 2003/0100512 A1 May 29, 2003

(30) Foreign Application Priority Data

Apr. 7, 2000 (GB) .................................. 0008710

(51) Int. Cl.
*A61K 38/06* (2006.01)
*A61K 38/05* (2006.01)
*C07K 5/04* (2006.01)
*C07K 5/06* (2006.01)

(52) U.S. Cl. .......................... 514/18; 514/19; 530/330; 530/331; 560/24; 560/159

(58) Field of Classification Search ................. 514/18, 514/19; 530/330, 331; 560/24, 169
See application file for complete search history.

(56) References Cited

U.S. PATENT DOCUMENTS 5,703,129 A 12/1997 Felsenstein et al.
6,252,041 B1 * 6/2001 Yanai et al. ................. 530/331

FOREIGN PATENT DOCUMENTS

| CA | 2076204 | * | 2/1993 |
| EP | 0356223 | | 2/1990 |
| WO | WO 94/13319 | | 6/1994 |

* cited by examiner

*Primary Examiner*—Christopher R. Tate
*Assistant Examiner*—Marcela M Cordero Garcia
(74) *Attorney, Agent, or Firm*—John C. Todaro; Melvin Winokur

(57) ABSTRACT

A class of compounds is disclosed which are diasteroisomers of a known class of protease inhibitors. The compound inhibit gamma-secretase, and find use in the treatment of and/or prevention of Alzheimer's disease.

8 Claims, No Drawings

GAMMA-SECRETASE INHIBITORS

CROSS REFERENCE TO RELATED APPLICATIONS

This application is a U.S. National Phase application under 35 U.S.C. § 371 of PCT Application No. PCT/GB01/01549, filed Apr. 4, 2001, which claims priority under 35 U.S.C. § 119 from GB Application No. 0008710.6, filed Apr. 7, 2000.

The present invention relates to compounds, their salts, pharmaceutical compositions comprising them, processes for making them and their use in treating Alzheimer's Disease.

Alzheimer's Disease (AD) is characterised by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The ragged $NH_2$- and COOH-termini of the native Aβ amyloid indicates that a complex mechanism of proteolysis is involved in its biogenesis.

The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

The compounds of the present invention are useful for treating AD by inhibiting the activity of the putative γ-secretase thus preventing the formation of insoluble Aβ and arresting the production of Aβ. Further, some of the present compounds also stabilise full-length presenilin-1.

In a further aspect some of the compounds of the present application are useful as inhibitors of presenilin-1 cleavage.

The compounds of the present invention are related to HIV protease inhibitors described in EP-A-337 714 and EP-A-356 223, both in the name of Merck & Co., Inc. These compounds are aspartyl protease inhibitors. Specifically, a subset of the compounds of the present invention differ from those previously described by the stereochemistry of a hydroxyl group which is a particularly preferred feature of the present invention and has not previously been disclosed for these particular compounds. This is a surprising feature giving rise to the present invention.

The present invention, in one aspect, provides a compound comprising the group:

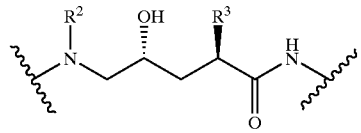

wherein $R^2$ and $R^3$ are as defined below, which compound is a diastereoisomer of a known protease inhibitor comprising the group

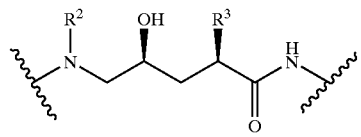

wherein $R^2$ and $R^3$ are as defined below.

The present invention accordingly provides a compound of formula I or a pharmaceutically acceptable salt thereof:

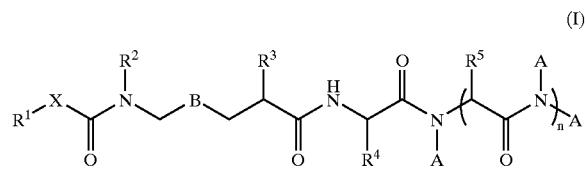

(I)

wherein:
$R^1$ is (1) $C_{1-10}$alkyl, $C_{2-10}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) —$NR^6R^7$ wherein $R^6$ and $R^7$ are independently chosen from hydrogen, $C_{1-5}$alkyl and $C_{1-5}$alkoxy $C_{1-5}$alkyl;
(vii) —$CONR^6R^7$ or $OCONR^6R^7$ wherein $R^6$ and $R^7$ are independently as defined above;
(viii) —$N(R^8)QR^9$ wherein:
  Q is C(O), C(S), $SO_2$ or C(NH);
  $R^8$ is hydrogen or $C_{1-4}$alkyl; and
  $R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl, (d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and
(k) $NR^8SO_2R^{8'}$ wherein $R^8$ and $R^{8'}$ are independently as defined above; or (2) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above, and
(k) $NR^8SO_2R^{8'}$ wherein $R^8$ and $R^{8'}$ are independently as defined above;

$R^2$ and $R^3$ are independently chosen from $C_{1-10}$alkyl, $C_{1-10}$alkoxy, $C_{2-10}$alkenyl, $C_{2-10}$alkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$ alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above;

alternatively $R^3$ may be hydrogen;

$R^4$ and $R^5$ are independently chosen from hydrogen, $C_{1-6}$alkyl optionally substituted by halogen, hydroxy, thiol, amino, $C_{1-4}$alkoxy, $C_{1-4}$ alkylthio, carboxy or $C_{1-4}$ alkoxycarbonyl, and $(CH_2)_qQ^2$ wherein $Q^2$ is a five-membered unsaturated heterocycle containing 1, 2, 3 or 4 heteroatoms optionally chosen from O, N, and S providing that not more than one heteroatom is O or S, a six-membered unsaturated heterocycle containing 1, 2 or 3 N atoms, phenyl or naphthyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$ and wherein each of the foregoing rings is optionally fused to a benzene ring; and A is:
(1) hydrogen;
(2) $C_{1-10}$alkyl, $C_{2-10}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) $—NR^6R^7$ wherein $R^6$ and $R^7$ are independently chosen from hydrogen, $C_{1-5}$alkyl and $C_{1-5}$alkoxy $C_{1-5}$alkyl;
(vii) $—CONR^6R^7$ or $OCONR^6R^7$ wherein $R^6$ and $R^7$ are independently as defined above;
(viii) $—N(R^8)QR^9$ wherein:
Q is $C(O)$, $C(S)$, $SO_2$ or $C(NH)$;
$R^8$ is hydrogen or $C_{1-4}$alkyl; and
$R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and (k) $NR^8SO_2R^{8'}$ wherein $R^8$ and $R^{8'}$ are independently as defined above; or (3) a seven-membered heterocycle having an otherwise unsubstituted carbon atom at the point of attachment to the rest of the compound of formula I, having at a first atom alpha to the point of attachment a carbon atom which is unsubstituted or substituted by an oxygen or sulphur atom, having at a first atom beta to the point of attachment, which atom is alpha to the foregoing first atom alpha, a carbon atom or a nitrogen atom, having at a second atom alpha to the point of attachment a carbon atom, which is optionally substituted by oxygen, or a nitrogen atom, having at a second atom beta to the point of attachment, which atom is alpha to the foregoing second atom alpha, a carbon atom or a nitrogen atom, and having at the two remaining atoms carbon atoms;

a double bond may be present between the second atom alpha and the second atom beta;

the seven-membered heterocycle may be fused to one or two aromatic rings via any adjacent pair of atoms other than the point of attachment and the first atom alpha alone or in combination;

the aromatic ring may be benzene or a five-membered heterocycle containing 1, 2, 3 or 4 heteroatoms chosen from O, N and S providing that not more than one heteroatom is O or S or a six-membered heterocycle containing 1, 2 or 3 nitrogen atoms;

alternatively a pair of adjacent carbon atoms in the seven-membered heterocycle, other than the point of attachment and the first atom alpha alone or in combination, may form part of a fused cyclopropyl or cyclopentyl ring;

one to three substitutable atoms of the seven-membered heterocycle are optionally substituted by:

an aromatic ring as defined above optionally substituted by hydroxy, halogen, methoxy or alkyl having one to four carbon atoms;

an alkyl group having one to four carbon atoms optionally substituted by a halogen atom, hydroxy, an aromatic ring as defined above optionally substituted by hydroxy, halogen, methoxy or alkyl having one to four carbon atoms, cycloalkyl having three to seven carbon atoms, methoxy, bicycloalkyl having seven to twelve carbon atoms, heterocycle having five to seven atoms one of which is oxygen, nitrogen or sulphur which is optionally oxidized;

a heterocycle having five to seven atoms one of which is oxygen, nitrogen or sulphur which is optionally oxidized;

cycloalkyl having three to seven carbon atoms;

or bicycloalkyl having seven to twelve carbon atoms;

or the two groups A attached to the same nitrogen atom, together with that atom, form: a five-membered heterocyclic ring optionally containing 1, 2 or 3 further heteroatoms chosen from O, N and S, not more than one of the heteroatoms being O or S; or a six-membered heterocyclic ring optionally containing 1 or 2 further nitrogen atoms; each of which is optionally substituted by one to three groups independently chosen from:

(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and
(k) $NR^8SO_2R^{8'}$ wherein $R^8$ and $R^{8'}$ are independently as defined above;

B is C=O or CHOH in the R configuration;

X is oxygen or a bond;

n is zero or one, and p is zero, one, two or three; and q is zero, one, two or three;

with the proviso that no carbon atom is substituted by more than one hydroxy group.

In an embodiment the compounds of the present invention are of formula I':

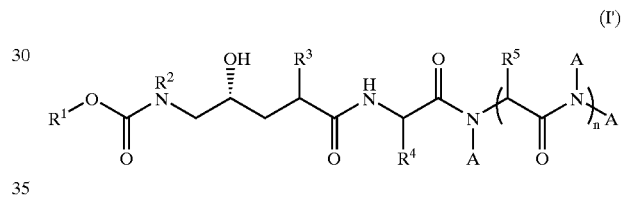

(I')

where $R^1$, $R^2$, $R^3$, $R^4$, $R^5$, A and n are as defined above.

In one embodiment the compounds of the present invention are of formula I":

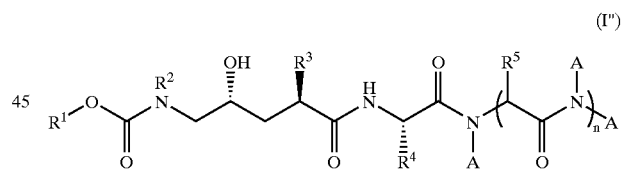

(I")

where $R^1$, $R^2$, $R^3$, $R^4$, $R^5$, A and n are as defined above.

In another embodiment there are provided compounds of formula I'":

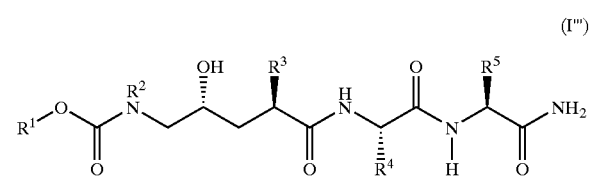

(I'")

where $R^1$, $R^2$, $R^3$, $R^4$ and $R^5$ are as defined above.

The following preferred definitions of substituents apply to each of the formulae I, I', I" and I'" which refer to those substituents.

Preferably R¹ is
(1) $C_{1-10}$alkyl, $C_{2-10}$alkenyl or $C_{2-10}$alkynyl optionally substituted with one to three substituents independently chosen from:
   (i) hydroxy;
   (ii) halogen;
   (iii) amino;
   (iv) $C_{1-4}$alkoxy; and
   (v) phenyl which is optionally substituted by one or two groups independently chosen from:
      (a) halogen, cyano and nitro,
      (b) hydroxy,
      (c) $C_{1-4}$alkyl, $C_{2-4}$alkenyl and $C_{2-4}$alkenyl,
      (d) $C_{1-4}$alkoxy and
      (e) amino; or
(2) phenyl which is optionally substituted by one or two groups independently chosen from:
   (a) halogen, cyano and nitro,
   (b) hydroxy,
   (c) $C_{1-4}$alkyl, $C_{2-4}$alkenyl and $C_{2-4}$alkynyl,
   (d) $C_{1-4}$alkoxy and
   (e) amino.

When R¹ is a heterocyclic ring it may be saturated, partially saturated or unsaturated. Preferably the heterocyclic ring is a heteroaromatic ring.

More preferably R¹ is $C_{1-10}$alkyl optionally substituted with up to three substituents as defined above. Even more preferably R¹ is $C_{1-6}$alkyl optionally substituted by one to three substituents as defined above. Most preferably R¹ is $C_{1-6}$alkyl optionally substituted by halogen, phenyl, hydroxy or $C_{1-4}$alkoxy. In particular R¹ may be tertiary butyl or benzyl, particularly tertiary butyl.

R² and R³ may be independently chosen from phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein Q¹ is phenyl; naphthyl; a five-membered heteroaromatic ring containing 1, 2, 3 or 4 heteroatoms independently chosen from O, N and S, at most one of the heteroatoms being O or S; and a six-membered heteroaromatic ring containing 1, 2 or 3 nitrogen atoms; and wherein each of R² and R³ is independently optionally substituted by one to three groups independently chosen from:
   (a) halogen, cyano and nitro,
   (b) hydroxy,
   (c) $C_{1-3}$alkyl, $C_{2-3}$alkenyl and $C_{2-3}$alkynyl,
   (d) $C_{1-3}$alkoxy,
   (e) NR⁶R⁷ wherein R⁶ and R⁷ are independently as defined above,
   (f) $CO_2R^8$ wherein R⁸ is independently as defined above,
   (g) CONR⁶R⁷ wherein R⁶ and R⁷ are independently as defined above,
   (h) $SO_2NR^6R^7$ wherein R⁶ and R⁷ are independently as defined above,
   (i) $CH_2NR^6R^7$ wherein R⁶ and R⁷ are independently as defined above,
   (j) N(R⁸)COR⁸' wherein R⁸ and R⁸' are independently as defined above,
   (k) $NR^8SO_2R^{8'}$ where R⁸ and R⁸' are independently as defined above;

More preferably R² and R³ are $(CH_2)_pQ^1$.
Preferably p is one or two.

Preferably Q¹ is phenyl optionally substituted by one or two groups independently chosen from:
   (a) halogen, cyano and nitro,
   (b) hydroxy,
   (c) $C_{1-4}$alkyl, $C_{2-4}$alkenyl and $C_{2-4}$alkynyl,
   (d) $C_{1-4}$alkoxy and
   (e) amino.

In one embodiment R² is phenethyl and R³ is benzyl.
More preferably Q¹ is phenyl.
Preferably R⁴ and R⁵ are independently chosen from optionally substituted $C_{1-6}$alkyl and $(CH_2)_qQ^2$. More preferably R⁴ and R⁵ are independently chosen from $C_{1-6}$alkyl and $(CH_2)_qQ^2$.
Preferably Q² is optionally substituted phenyl. More preferably Q² is phenyl.
In particular R⁴ and R⁵ are independently chosen from methyl, benzyl, phenyl, 2-methylpropyl, 1-hydroxyethyl, isopropyl and isobutyl. R⁴ may be isobutyl. R⁵ may be benzyl.

A is preferably hydrogen or a group

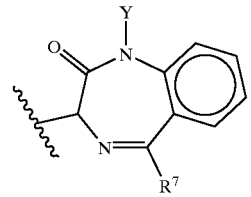

wherein R⁷ is phenyl, $C_{1-6}$alkyl or $C_{3-7}$cycloalkyl and Y is hydrogen or $C_{1-6}$ alkyl. More preferably A is hydrogen or a group as defined above wherein R⁷ is a cyclohexyl group. A may be hydrogen.

X is preferably oxygen.
n may be one.
p is preferably one.
q is preferably zero or one.

Thus a subclass of compounds of formula I and I' is provided wherein:
R¹ is
(1) $C_{1-10}$alkyl, $C_{2-10}$alkenyl or $C_{2-10}$alkynyl optionally substituted with one or more substituents independently chosen from:
   (i) hydroxy;
   (ii) halogen;
   (iii) amino;
   (iv) $C_{1-4}$alkoxy; and
   (v) phenyl which is optionally substituted by one or two groups independently chosen from:
      (a) halogen, cyano and nitro,
      (b) hydroxy,
      (c) $C_{1-4}$alkyl, $C_{2-4}$alkenyl and $C_{2-4}$alkynyl,
      (d) $C_{1-4}$alkoxy and
      (e) amino; or
(2) phenyl which is optionally substituted by one or two groups independently chosen from:
   (a) halogen, cyano and nitro,
   (b) hydroxy,
   (c) $C_{1-4}$alkyl, $C_{2-4}$alkenyl and $C_{2-4}$alkynyl,
   (d) $C_{1-4}$alkoxy and
   (e) amino;

$R^2$ and $R^3$ are both $(CH_2)_pQ^1$ wherein $Q^1$ is phenyl optionally substituted by one or two groups independently chosen from:
(a) halogen,
(b) hydroxy,
(c) $C_{1-4}$alkyl, $C_{2-4}$alkenyl and $C_{2-4}$alkynyl,
(d) $C_{1-4}$alkoxy and
(e) amino;

$R^4$ and $R^5$ are independently chosen from $C_{1-6}$alkyl optionally substituted by halogen, hydroxy, amino or $C_{1-4}$alkoxy and $(CH_2)_qQ^2$ wherein $Q^2$ is phenyl optionally substituted by hydroxy, $C_{1-4}$alkyl, $C_{1-4}$alkoxy, thiol, $C_{1-4}$alkylthio, halogen, amino, carboxy, amido, $CO_2H$ and $-NHC(NH_2)_2$;

A is hydrogen or

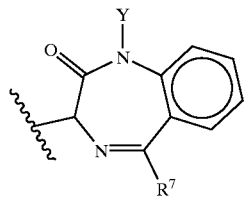

wherein $R^7$ is phenyl, $C_{1-6}$alkyl or $C_{3-7}$cycloalkyl;
Y is hydrogen or $C_{1-6}$ alkyl;
n is zero or one;
p is one; and
q is zero or one.

For the avoidance of doubt each time the moieties A, $R^6$, $R^7$, $R^8$, $R^{8'}$ and $R^9$ occur more than once in the definition of the compounds of formula (I) they are chosen independently.

As used herein, the expression "$C_{1-10}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-6}$alkyl", "$C_{1-4}$alkyl", "$C_{2-10}$alkenyl", "$C_{2-4}$alkenyl", "$C_{2-10}$alkynyl" and "$C_{2-4}$alkynyl" are to be construed in an analogous manner.

The expression "$C_{3-7}$cycloalkyl" as used herein includes cyclic propyl, butyl, pentyl, hexyl and heptyl groups such as cyclopropyl and cyclohexyl.

The term "heterocyclic" includes rings which are saturated, partially saturated or unsaturated. Unsaturated heterocyclic rings are also known as heteroaromatic rings.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. Suitable saturated heterocyclic rings include piperazine, morpholine, piperidine, tetrahydrofuran and tetrahydrothiophene. Tetrahydrofuran is preferred.

The term "halogen" as used herein includes fluorine, chlorine, bromine and iodine, of which fluorine and chlorine are preferred.

As used herein the term "$C_{1-4}$alkoxy" includes methoxy and ethoxy groups, and straight-chained, branched and cyclic propoxy and butoxy groups, including cyclopropylmethoxy.

A specific Examples according to the present invention is: {4R-[1S-(1-carbamoyl-2-phenyl-ethylcarbamoyl)-3(1S)-methylbutylcarbamoyl]-2R-hydroxy-5-phenylpentyl}phenethyl-carbamic acid tert-butyl ester and the pharmaceutically acceptable salts thereof.

Examples of pharmaceutically acceptable salts are hydrochlorides, sulfates, citrates, tartrates, acetates, methanesulfonates, phosphates, oxalates and benzoates.

The compounds of the present invention have an activity as inhibitors of γ secretase. In a preferred embodiment the compounds of the invention inhibit proteolysis of PS-1.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

There is also provided a process for producing a compound of formula I or a pharmaceutically acceptable salt thereof which comprises reacting a compound of formula II with a compound of formula III:

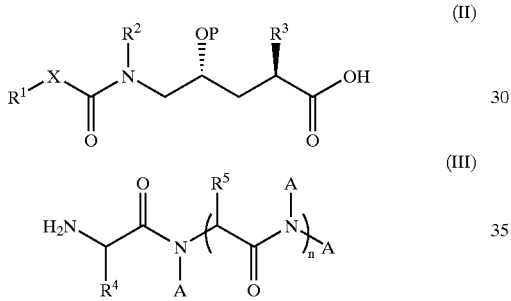

wherein $R^1$, $R^2$, $R^3$, $R^4$, $R^5$, A, X and n are as defined above and P is hydrogen or a protecting group such as a trialkylsilane group, for example t-butyl dimethylsilyl, followed, if necessary, by deprotection of the resulting compound to produce a compound of formula I. The reaction is generally carried out in the presence of coupling agents such as 1-(3-dimethylaminopropyl)-3-ethylcarbodiimide hydrochloride and 1-hydroxybenzotriazole in a solvent such as DMF, generally at about room temperature for six to twelve hours. Any necessary deprotection is achieved by conventional means.

The compound of formula II is produced by reacting a compound of formula IV:

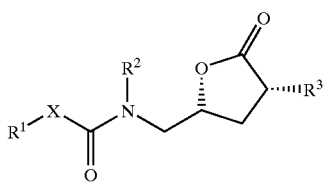

wherein $R^1$, $R^2$, $R^3$ and X are as defined above in a solvent such as dioxane, with a base such as lithium hydroxide in a polar solvent such as water generally at room temperature for above five hours. If desired the resulting compound of formula II in which P is hydrogen is protected by conventional means.

The compound of formula IV is produced by reacting a compound of formula V with a compound of formula VI:

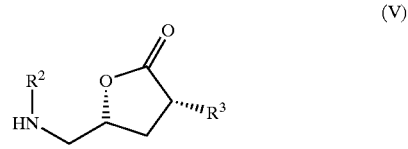

wherein $R^1$, $R^2$, $R^3$ and X are as defined above and L is a leaving group such as halogen, O-alkyl or O-acyl, generally in a solvent such as dichloromethane at room temperature for about 2 h.

The compound of formula V is produced by reacting a compound of formula VII with a compound of formula VIII:

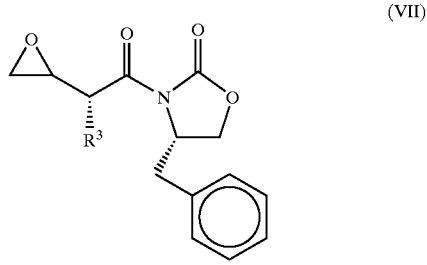

wherein $R^2$ and $R^3$ are as defined above generally in a solvent such as isopropanol generally with heating to about 60° C. for several hours.

Compounds of formula VII may be prepared by methods known in the art, for example in Biorg. Med. Chem. Lett. 1994, 903.

Compounds of formulae III, VI and VIII are commercially available or known in the prior art or can be made from commercially available or known compounds by standard methods.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. In particular the lactone ring of the compound of formula IV may be a mixture of diastereoisomers. In this case diastereomeric separation occurs at some point in the process. Alternatively the mixture of the final product, the compound of formula I and its diastereomer, may be reacted with an oxidizing agent such as pyridinium chlorochromate and then reduced with a reducing agent such as sodium borohydride in an attempt to increase the amount of the desired diastereomer prior to separation by, for example, HPLC.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.
(2) Cells are placed in 96-well plates at 30,000/well/100 µL in minimal essential medium (MEM) (phenol red-free) +10% foetal bovine serum (FBS), 50 mM HEPES buffer (pH 7.3), 1% glutamine, 0.2 mg/mL G418 antibiotic, 10 mM sodium butyrate.
(3) Make dilutions of the compound plate. Dilute stock solution to 5.5% DMSO/110 µM compound. Mix compounds vigorously and store at 4° C. until use.
(4) Add 10 µL compound/well. Mix plate briefly, and leave for 18 h in 37° C. incubator.
(5) Remove 90 µL of culture supernatant and dilute 1:1 with ice-cold 25 mM HEPES (pH0.3), 0.1% BSA, 1.0 mM EDTA (+broad spectrum protease inhibitor cocktail; pre-aliquotted into a 96-well plate). Mix and keep on ice or freeze at −80° C.
(6) Add back 100 µL of warm MEM+10% FBS, 50 mM HEPES (pH7.3), 1% glutamine, 0.2 mg/mL G418, 10 mM sodium butyrate to each well, and return plate to 37° C. incubator.
(7) Prepare reagents necessary to determine amyloid peptide levels, for example by ELISA assay
(8) To determine if compounds are cytotoxic cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 µL/well MTS/PES solution to the cells; mix and leave at 37° C.
(11) Read plate when the absorbance values are approximately 1.0 (mix briefly before reading to disperse the reduced formazan product).

The Examples of the present invention all had an $ED_{50}$ of less than 500 nM, preferably less than 200 nM and most preferably less than 100 nM in the above assay.

The following examples illustrate the present invention.

EXAMPLE 1

{4R-[1S-(1-carbamoyl-2-phenyl-ethylcarbamoyl)-3 (1S)-methylbutylcarbamoyl]-2R-hydroxy-5-phenypentyl}phenethylcarbamic acid tert-butyl ester Step 1: (4R-benzyl-5-oxo-tetrahydrofuran-2(R,S)-ylmethyl)-phenethylcarbamic acid tert-butyl ester A solution of 4S-benzyl-3-(2R-oxiranyl-3-phenylpropionyl)-oxazolidin-2-one (A) (Trova et al, *Bioorg. Med. Chem. Lett.*, 1994, 4, 903) (300 mg) in isopropanol (5 ml) was treated with 2-phenethylamine (110 µl) and heated at 60° C. overnight. The reaction mixture was evaporated under reduced pressure and purified by flash column chromatography on silica gel. The resulting lactone was dissolved in dichloromethane and treated with di-tert-butyl dicarbonate (200 mg) and stirred at room temperature for 2 h. The reaction mixture was evaporated in vacuo to give (4R-benzyl-5-oxotetrahydrofuran-2(R,S)-ylmethyl)phenethylcarbamic acid tert-butyl ester (B) (160 mg, 47%) as a white solid.

Step 2: 2R-benzyl-5-(tert-butoxycarbonylphenethylamino)-4(R,S)-(tert-butyldimethylsilanyloxy)pentanoic acid A solution of (4R-benzyl-5-oxotetrahydrofuran-2(R,S)-ylmethyl)-phenethylcarbamic acid tert-butyl ester (B) (120 mg) in dioxane (3 ml) was treated with a solution of $LiOH.H_2O$ in $H_2O$ (1.0M, 2.9 ml) and stirred at room temperature for 2 h. The reaction mixture was acidified with citric acid and extracted with ethyl acetate twice. The combined organic extracts were washed with brine, dried ($MgSO_4$), filtered and evaporated under reduced pressure. The resulting crude hydroxyacid was dissolved in DMF (5 ml) and treated with TBSCl (443 mg) and imidazole (239 mg) and stirred over the weekend at room temperature. The reaction mixture was treated with methanol and stirred for 2 h. The reaction mixture was purified by flash column chromatography to give 2R-benzyl-5-(tert-butoxycarbonylphenethylamino)-4(R,S)-(tert-butyldimethyl-silanyloxy)pentanoic acid (C) (120 mg, 76%).

Step 3: {4R-[1S-(1-carbamoyl-2-phenylethylcarbamoyl)-3(1S)-methylbutylcarbamoyl]-2(R,S)-hydroxy-5-phenylpentyl}phenethylcarbamic acid tert-butyl ester A solution of 2R-benzyl-5-(tert-butoxycarbonylphenethylamino)-4(R,S)-(tert-butyldimethylsilanyloxy)pentanoic acid (C) (64 mg) in DMF (1 ml) was treated with $H_2N$-Leu-Phe-$CONH_2$ (39 mg), 1-hydroxybenzotriazole (19 mg), and EDC (27 mg) and stirred at room temperature overnight. The reaction mixture was diluted with ethyl acetate, and washed with aqueous citric acid, aqueous $NaHCO_3$ solution and brine, dried ($MgSO_4$), filtered and evaporated under reduced pressure. This product was dissolved in TBAF (1.0 M in THF, 2 ml) and stirred at room temperature for 3 h. The reaction mixture was diluted with citric acid and brine and ethyl acetate. The organic layer was separated, dried ($MgSO_4$), filtered and evaporated in vacuo to give the product {4R-[1S-(1-carbamoyl-2-phenylethylcarbamoyl)-3 (1S)-methylbutylcarbamoyl]-2(R,S)-hydroxy-5-phenylpentyl}phenethylcarbamic acid tert-butyl ester (D) (40 mg, 63%).

Step 4E: {4R-[1S-(1-carbamoyl-2-phenyl-ethylcarbamoyl)-3(1S)-methylbutylcarbamoyl]-2R-hydroxy-5-phenylpentyl}phenethylcarbamic acid tert-butyl ester A solution of {4R-[1S-(1-carbamoyl-2-phenylethylcarbamoyl)-3(1S)-methylbutylcarbamoyl]-2(R,S)-hydroxy-5-phenylpentyl}phenethylcarbamic acid tert-butyl ester (D) (50 mg) in dichloromethane (2 ml) was treated with 4 A molecular sieves (31 mg), cooled to 0° C. and treated with pyridinium chlorochromate (31 mg) and stirred for 1 h. More pyridinium chlorochromate (30 mg) and molecular sieves (100 mg) were added and stirred for two days. The reaction mixture was diluted with ethyl acetate, filtered and purified by flash column chromatography to give the intermediate ketone. This was dissolved in ethanol (2 ml), cooled to 0° C. and treated with NaBH$_4$ (3 mg) and warmed to room temperature. The reaction mixture was stirred overnight, then dissolved in ethyl acetate and aqueous ammonium chloride solution. The organic layer was separated, washed with brine, dried (MgSO$_4$), filtered and evaporated under reduced pressure. Purification by flash column chromatography and reverse-phase HPLC (eluting with acetonitrile-water 70:30) gave {4R-[1S-(1-carbamoyl-2-phenyl-ethylcarbamoyl)-3(1S)-methylbutylcarbamoyl]-2R-hydroxy-5-phenylpentyl}phenethylcarbamic acid tert-butyl ester (E) (1H NMR, 400 MHz, DMSO, 340 K) 7.66 (1H, d, J=7.7), 7.43 (1H, d, J=8.2), 7.28–7.09 (17H, m), 4.45–4.39 (2H, m), 4.18–4.13 (1H, m), 3.62–3.60 (1H, m), 3.40–3.30 (2H, m), 3.10–2.48 (9H, m), 1.62–1.37 (5H, m), 1.35 (9H, s), 0.80 (3H, d, J= 6.6), 0.76 (3H, d, J=6.6). m/z: Found 687 (MH$^+$), C40H54N4O6+H$^+$ requires 687.

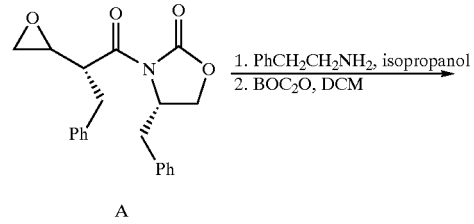

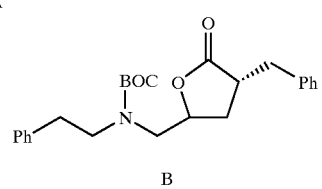

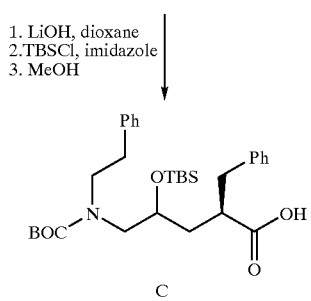

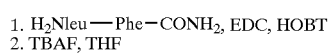

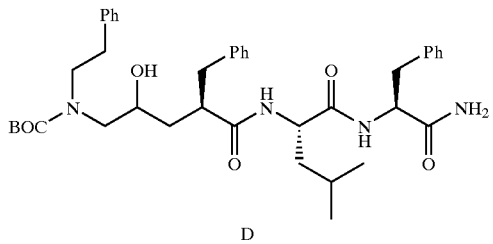

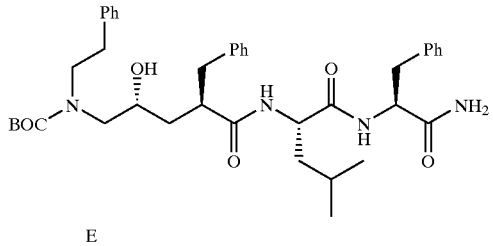

D

1. PCC, 4A MS, DCM
2. NaBH$_4$, MeOH
3. HPLC

E

What is claimed is:
1. A compound of formula I or a pharmaceutically acceptable salt thereof:

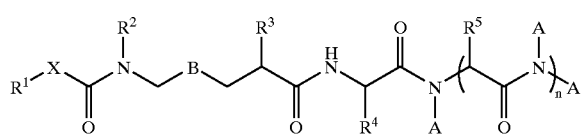

(I)

wherein:
R$^1$ is (1) C$_{1-10}$alkyl, C$_{2-10}$alkenyl or C$_{2-10}$alkynyl optionally substituted with one to three substituents independently chosen from:
(i) hydroxy;
(ii) carboxy;
(iii) halogen;
(iv) C$_{1-4}$alkoxy;
(v) C$_{1-4}$alkoxycarbonyl;
(vi) —NR$^6$R$^7$ wherein R$^6$ and R$^7$ are independently chosen from hydrogen, C$_{1-5}$alkyl and C$_{1-5}$alkoxy C$_{1-5}$alkyl;
(vii) —CONR$^6$R$^7$ or OCONR$^6$R$^7$ wherein R$^6$ and R$^7$ are independently as defined above;
(viii) —N(R$^8$)QR$^9$ wherein:
Q is C(O), C(S), SO$_2$ or C(NH);
R$^8$ is hydrogen or C$_{1-4}$alkyl; and
R$^9$ is hydrogen, C$_{1-4}$alkyl, C$_{1-4}$alkoxy, amino, C$_{1-4}$alkylamino di(C$_{1-4}$alkyl)amino wherein each alkyl group is independently chosen;
(ix) C$_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$, and
(k) $NR^8SO_2R^{8'}$ wherein $R^8$ and $R^{8'}$ are independently as defined above; or
(2) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above, and
(k) $NR^8SO_2R^{8'}$ wherein $R^8$ and $R^{8'}$ are independently as defined above;
$R^2$ and $R^3$ are independently chosen from $C_{1-10}$alkyl, $C_{1-10}$alkoxy, $C_{2-10}$alkenyl, $C_{2-10}$alkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are in independently as defined above,
(k) $NR^8SO_2R^{8'}$ where $R^8$ and $R^{8'}$ are independently as defined above;
alternatively $R^3$ may be hydrogen;
$R^4$ and $R^5$ are independently chosen from hydrogen, $C_{1-6}$alkyl optionally substituted by halogen, hydroxy, thiol, amino, $C_{1-4}$alkoxy, $C_{1-4}$ alkylthio, carboxy or $C_{1-4}$ alkoxycarbonyl, and $(CH_2)_qQ^2$ wherein $Q^2$ is a five-membered unsaturated heterocycle containing 1, 2, 3 or 4 heteroatoms optionally chosen from O, N, and S providing that not more than one heteroatom is O or S, a six-membered unsaturated heterocycle containing 1, 2 or 3 N atoms, phenyl or naphthyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$ and wherein each of the foregoing rings is optionally fused to a benzene ring; and
A is:
(1) hydrogen;
(2) $C_{1-10}$alkyl, $C_{2-10}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) $—NR^6R^7$ wherein $R^6$ and $R^7$ are independently chosen from hydrogen, $C_{1-5}$alkyl and $C_{1-5}$alkoxy $C_{1-5}$alkyl;
(vii) $—CONR^6R^7$ or $OCONR^6R^7$ wherein $R^6$ and $R^7$ are independently as defined above;
(viii) $—N(R^8)QR^9$ wherein:
Q is C(O), C(S), $SO_2$ or C(NH);
$R^8$ is hydrogen or $C_{1-4}$alkyl; and
$R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above, (h) SO$_2$NR$^6$R$^7$ wherein R$^6$ and R$^7$ are independently as defined above,
(i) CH$_2$NR$^6$R$^7$ wherein R$^6$ and R$^7$ are independently as defined above,
(j) N(R$^8$)COR$^{8'}$ wherein R$^8$ is independently as defined above and R$^{8'}$ is independently as defined for R$^8$, and
(k) NR$^8$SO$_2$R$^{8'}$ wherein R$^8$ and R$^{8'}$ are independently as defined above; or (3) a seven-membered heterocycle
  having an otherwise unsubstituted carbon atom at the point of attachment to the rest of the compound of formula I,
  having at a first atom alpha to the point of attachment a carbon atom which is unsubstituted or substituted by an oxygen or sulphur atom,
  having at a first atom beta to the point of attachment, which atom is alpha to the foregoing first atom alpha, a carbon atom or a nitrogen atom,
  having at a second atom alpha to the point of attachment a carbon atom, which is optionally substituted by oxygen, or a nitrogen atom,
  having at a second atom beta to the point of attachment, which atom is alpha to the foregoing second atom alpha, a carbon atom or a nitrogen atom,
  and having at the two remaining atoms carbon atoms;
  a double bond may be present between the second atom alpha and the second atom beta;
  the seven-membered heterocycle may be fused to one or two aromatic rings via any adjacent pair of atoms other than the point of attachment and the first atom alpha alone or in combination;
  the aromatic ring may be benzene or a five-membered heterocycle containing 1, 2, 3 or 4 heteroatoms chosen from O, N and S providing that not more than one heteroatom is O or S or a six-membered heterocycle containing 1, 2 or 3 nitrogen atoms;
  alternatively a pair of adjacent carbon atoms in the seven-membered heterocycle, other than the point of attachment and the first atom alpha alone or in combination may form part of a fused cyclopropyl or cyclopentyl ring;
  one to three substitutable atoms of the seven-membered heterocycle are optionally substituted by:
    an aromatic ring as defined above optionally substituted by hydroxy, halogen, methoxy or alkyl having one to four carbon atoms;
    an alkyl group having one to four carbon atoms optionally substituted by a halogen atom, hydroxy, an aromatic ring as defined above optionally substituted by hydroxy, halogen, methoxy or alkyl having one to four carbon atoms, cycloalkyl having three to seven carbon atoms, methoxy, bicycloalkyl having seven to twelve carbon atoms, heterocycle having five to seven atoms one of which is oxygen, nitrogen or sulphur which is optionally oxidized; a heterocycle having five to seven atoms one of which is oxygen, nitrogen or sulphur which is optionally oxidized;
    cycloalkyl having three to seven carbon atoms;
    or bicycloalkyl having seven to twelve carbon atoms;
    or the two groups A attached to the same nitrogen atom, together with that atom, form: a five-membered heterocyclic ring optionally containing 1, 2 or 3 further heteroatoms chosen from O, N and S, not more than one of the heteroatoms being O or S; or a six-membered heterocyclic ring optionally containing 1 or 2 further nitrogen atoms; each of which is optionally substituted by one to three groups independently chosen from:
  (a) halogen, cyano and nitro,
  (b) hydroxy,
  (c) C$_{1-4}$alkyl, C$_{2-4}$alkenyl and C$_{2-4}$alkynyl,
  (d) C$_{1-4}$alkoxy,
  (e) NR$^6$R$^7$ wherein R$^6$ and R$^7$ are independently as defined above,
  (f) CO$_2$R$^8$ wherein R$^8$ is independently as defined above,
  (g) CONR$^6$R$^7$ or OCONR$^6$R$^7$ wherein R$^6$ and R$^7$ are independently as defined above,
  (h) SO$_2$NR$^6$R$^7$ wherein R$^6$ and R$^7$ are independently as defined above,
  (i) CH$_2$NR$^6$R$^7$ wherein R$^6$ and R$^7$ are independently as defined above,
  (j) N(R$^8$)COR$^{8'}$ wherein R$^8$ is independently as defined above and R$^{8'}$ is independently as defined for R$^8$, and
  (k) NR$^8$SO$_2$R$^{8'}$ wherein R$^8$ and R$^{8'}$ are independently as defined above;

B is C=O or CHOH in the R configuration;
X is oxygen or a bond;
n is zero or one, and
p is zero, one, two or three; and
q is zero, one, two or three;
with the proviso that no carbon atom is substituted by more than one hydroxy group.

2. A compound according to claim 1 of formula I':

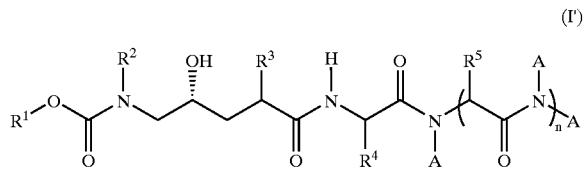

(I')

or a pharmaceutically acceptable salt thereof.

3. A compound according to claim 2 of formula I":

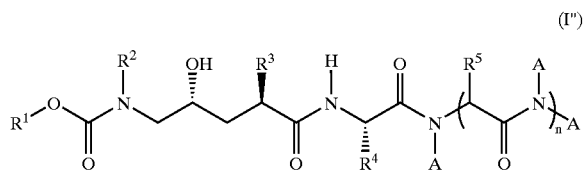

(I")

or a pharmaceutically acceptable salt thereof.

4. A compound according to claim 3 of formula I'":

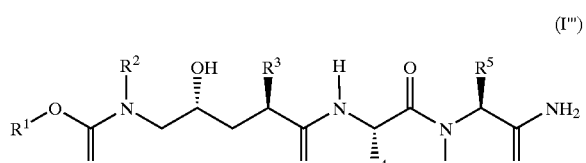

(I'")

or a pharmaceutically acceptable salt thereof.

5. A compound according to claim 1 or claim 2 wherein:
R$^1$ is
(1) C$_{1-10}$alkyl, C$_{2-10}$alkenyl or C$_{2-10}$alkynyl optionally substituted with one or more substituents independently chosen from:
   (i) hydroxy;
   (ii) halogen;
   (iii) amino;
   (iv) C$_{1-4}$alkoxy; and
   (v) phenyl which is optionally substituted by one or two groups independently chosen from:
      (a) halogen, cyano and nitro,
      (b) hydroxy,
      (c) C$_{1-4}$alkyl, C$_{2-4}$alkenyl and C$_{2-4}$alkynyl,
      (d) C$_{1-4}$alkoxy and
      (e) amino; or
(2) phenyl which is optionally substituted by one or two groups independently chosen from:
   (a) halogen, cyano and nitro,
   (b) hydroxy,
   (c) C$_{1-4}$alkyl, C$_{2-4}$alkenyl and C$_{2-4}$alkynyl,
   (d) C$_{1-4}$alkoxy and
   (e) amino;
R$^2$ and R$^3$ are both (CH$_2$)$_p$Q$^1$ wherein Q$^1$ is phenyl optionally substituted by one or two groups independently chosen from:
   (a) halogen,
   (b) hydroxy,
   (c) C$_{1-4}$alkyl, C$_{2-4}$alkenyl and C$_{2-4}$alkynyl,
   (d) C$_{1-4}$alkoxy and
   (e) amino;
R$^4$ and R$^5$ are independently chosen from C$_{1-6}$alkyl optionally substituted by halogen, hydroxy, amino or C$_{1-4}$alkoxy and (CH$_2$)$_q$Q$^2$ wherein Q$^2$ is phenyl optionally substituted by hydroxy, C$_{1-4}$alkyl, C$_{1-4}$alkoxy, thiol, C$_{1-4}$alkylthio, halogen, amino, carboxy, amido, CO$_2$H and —NHC(NH$_2$)$_2$;
A is hydrogen or

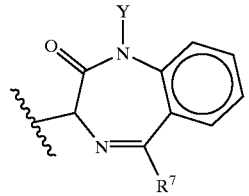

wherein R$^7$ is phenyl, C$_{1-6}$alkyl or C$_{3-7}$cycloalkyl;
Y is hydrogen or C$_{1-6}$ alkyl;
n is zero or one;
p is one; and
q is zero or one;
or a pharmaceutically acceptable salt thereof.

6. A compound according to claim 5 which is {4R-[1S-(1-carbamoyl-2-phenyl-ethylcarbamoyl)-3(1S)-methylbutylcarbamoyl]-2R-hydroxy-5-phenylpentyl}phenethyl-carbamic acid tert-butyl ester or a pharmaceutically acceptable salt thereof.

7. A pharmaceutical composition comprising the compound of claim 1 and a pharmaceutically acceptable carrier.

8. A method of treatment of a subject suffering from or prone to Alzheimer's disease which comprises administering to that subject an effective amount of a compound according to claim 1.

* * * * *